United States Patent
Pung et al.

(10) Patent No.: US 6,753,063 B1
(45) Date of Patent: Jun. 22, 2004

(54) PERSONAL CLEANSING WIPE ARTICLES HAVING SUPERIOR SOFTNESS

(75) Inventors: David John Pung, Maineville, OH (US); Steven Kirk Hedges, Fairfield, OH (US); Frank Lin, Loveland, OH (US); Marcus Wayne Evans, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/186,902

(22) Filed: Nov. 6, 1998

Related U.S. Application Data

(60) Provisional application No. 60/066,207, filed on Nov. 19, 1997.

(51) Int. Cl.[7] ............................. D06N 7/04; B32B 3/00; B32B 1/00; B32B 27/04; B32B 27/12; D04H 3/10; D04H 5/02; D04H 13/00; D04H 18/00
(52) U.S. Cl. ....................... 428/152; 428/156; 428/187; 442/123; 442/408; 15/104.93; 28/105
(58) Field of Search ........................... 442/59, 123, 408; 428/152, 187, 156; 15/104.93; 28/105

(56) References Cited

U.S. PATENT DOCUMENTS

| | | | | |
|---|---|---|---|---|
| 3,485,706 A | | 12/1969 | Evans ........................ 161/72 |
| 4,191,609 A | | 3/1980 | Trokhan ..................... 162/113 |
| 4,755,421 A | * | 7/1988 | Manning et al. ............ 428/224 |
| 5,073,235 A | | 12/1991 | Trokhan ..................... 162/199 |
| 5,098,764 A | | 3/1992 | Bassett et al. .............. 428/131 |
| 5,141,803 A | * | 8/1992 | Pregozen .................... 428/288 |
| 5,213,588 A | | 5/1993 | Wong et al. .................. 51/293 |
| 5,648,083 A | | 7/1997 | Blieszner et al. ........... 424/402 |
| 5,670,234 A | | 9/1997 | Suehr et al. ................ 428/131 |
| 5,674,587 A | | 10/1997 | James et al. ................ 428/131 |
| 5,674,591 A | * | 10/1997 | James et al. ................ 428/156 |
| 5,763,332 A | * | 6/1998 | Gordon et al. ................ 442/84 |
| 5,871,762 A | | 2/1999 | Venkitaraman et al. ..... 424/402 |

FOREIGN PATENT DOCUMENTS

| | | | |
|---|---|---|---|
| EP | 0 418 493 A1 | 3/1991 | ............ D04H/1/44 |
| EP | 0 483 816 A1 | 5/1992 | ............ D04H/1/44 |
| EP | 0 750 063 A1 | 12/1995 | ............ D04H/1/46 |
| JP | 58-132155 A | 8/1983 | |
| JP | 63-175990 U | 11/1988 | |
| JP | 06-294059 A | 10/1994 | |
| JP | 07-250779 A | 3/1995 | |
| WO | WO 96/02701 | 2/1996 | ............ D21F/11/00 |
| WO | WO 96/14457 | 5/1996 | ............ D04H/1/46 |
| WO | WO 96/37652 | 11/1996 | ............ D06L/1/04 |
| WO | WO98/18441 | 5/1998 | ............ A61K/7/50 |

\* cited by examiner

*Primary Examiner*—Elizabeth M. Cole
*Assistant Examiner*—Jeremy R. Pierce
(74) *Attorney, Agent, or Firm*—Cynthia L. Clay; John M. Howell; Marianne Dressman

(57) ABSTRACT

The present invention relates to personal cleansing wipes articles which have superior softness, feel and cleansing properties. The wipes of the present invention comprise a substrate and an aqueous liquid cleansing composition which is coated onto or impregnated into said substrate to the extent of from about 100% to about 400% by weight of the substrate. The substrate is a single-layer, nonwoven substrate which is formed from hydroentangled fibers. Upon a substantial portion of a base surface comprising the substrate there exists a three-dimensional pattern comprising a plurality of discrete, raised fibrous regions. The raised fibrous regions have a density which is substantially the same as the density of the base surface. The raised fibrous regions are joined to the base surface by a fibrous transition region. The aqueous liquid cleansing composition comprises an effective amount of a cleansing surfactant.

8 Claims, No Drawings

PERSONAL CLEANSING WIPE ARTICLES HAVING SUPERIOR SOFTNESS

This application claims benefit of provisional application 60/066,207, filed on Nov. 19, 1997.

TECHNICAL FIELD

The present invention relates to personal cleansing wipe articles which have superior softness, feel and cleansing properties. The personal cleansing wipes of the present invention comprise a single layer, nonwoven, hydroentangled substrate and an aqueous liquid cleansing composition coated onto or impregnated into the substrate.

BACKGROUND OF THE INVENTION

Consumers have in the past used absorbent sheets impregnated with topical compositions for a variety of purposes. For example, wipes impregnated with cleansing compositions are frequently used to conveniently wash hands and face while traveling or in public or anytime when water and soap are not readily accessible. Such wipes are also frequently used on babies to clean up after a bowel movement.

Some consumers have indicated a desire that personal cleansing wipes, baby wipes or other wipes for use on human skin feel softer to the skin than wipes which are currently commercially available. Applicants have now found that softer wipes compositions can be provided by utilizing particular nonwoven, patterned substrates made from hydroentangled fibers in combination with an aqueous cleansing composition.

Substrates which are made from hydroentangled fibers are well known in the art. See, for example, Evans; U.S. Pat. No. 3,485,706; issued Dec. 23, 1969. Patterned substrates are also known in the art. The prior art describes two basis ways of forming a pattern on a nonwoven substrate: mechanical embossing and aperturing. Patterned substrates produced by these prior art methods are associated with consumer-negative. Mechanical embossing involves the application of force to a web through rigid members, such as protrusions on the periphery of a roll, to create areas of high density in the substrate, without changing the basis weight of the high density areas. Unfortunately, the mechanical embossing process can provide a pattern at the expense of other properties desired by the consumer. In particular, embossing can disrupt the bonds between fibers, thereby reducing the tensile strength of the web. Additionally, the pattern may not remain intact when the substrate is wetted. Aperturing involves the creation of a network of fiber bundles around a series of holes or apertures. These patterns are not three-dimensional, raised portions do not exist on the sheet. Although providing a visual effect, this type of pattern does not result in increased softness to the substrate.

It is an object of the present invention to provide wipes articles which arm impregnated with an aqueous cleansing composition which have superior softness, feel and cleaning properties compared to prior art compositions.

It is further an object of the present invention to accomplish superior softness, feel and cleansing without incurring consumer-negatives with respect to other aspects of the wipes article.

SUMMARY OF THE INVENTION

The present invention relates to personal cleansing wipes articles which have superior softness, feel and cleansing properties. The wipes of the present invention comprise a substrate and an aqueous liquid cleansing composition which is coated onto or impregnated into said substrate to the extent of from about 100% to about 400% by weight of the substrate. The substrate is a single-layer, nonwoven substrate which is formed from hydroentangled fibers. Upon a substantial portion of a base surface comprising the substrate there exists a three-dimensional pattern comprising a plurality of discrete, raised fibrous regions. The raised fibrous regions have a density which is substantially the same as the density of the base surface. The raised fibrous regions are joined to the base surface by a fibrous transition region. The aqueous liquid cleansing composition comprises an effective amount of a cleansing surfactant.

DETAILED DESCRIPTION OF THE INVENTION

The present invention relates to personal cleansing wipes articles which have superior softness, feel and cleansing properties. As used herein, the term "personal cleansing wipes article" refers to products in which a sheet of porous or absorbent material has been impregnated with a personal cleansing composition for the purpose of rubbing the wipe product over a surface (e.g. skin) to clean the surface. The personal cleansing wipes articles of the present invention comprise a particular substrate and a liquid aqueous cleansing composition which is coated onto or impregnated into the substrate. The ingredients used to prepare the personal cleansing wipes articles of the present invention, as well as process for preparing them, are described in detail as follows:

I. Ingredients

A. The Substrate

The personal cleansing wipes compositions of the present invention comprise a single layer, nonwoven substrate formed from hydroentangled fibers. By "nonwoven" is meant that the substrate is comprised of fibers which are not woven into a fabric but rather are formed into a sheet, mat, or pad layer having suitable basis weight, caliper, absorbency and strength characteristics.

The fibers from which the substrate is formed can be natural, synthetic, or mixtures thereof. Suitable natural fibers from which to prepare the substrates herein include, for example, wood pulp, wool, silk, jute, hemp, cotton, linen, sisal, ramie and mixtures thereof. Suitable synthetic fibers from which the substrates herein can be prepared include rayon, cellulose ester, polyvinyl derivatives, polyolefins, polyamides, acetate, acrylic, modacrylic fibers, polyester, polyurethane foam, and mixtures thereof. Specific examples of some of these synthetic materials include acrylics such as acrilan, creslan, and the acrylonitrile-based fiber, orlon; cellulose ester fibers such as cellulose acetate, amel, and acele; polyamides such as nylons (e.g., nylon 6, nylon 66. nylon 610, and the like); polyesters such as fortrel, kodel, and the polyethylene terephthalate fiber, dacron; polyolefins such as polypropylene, polyethylene; polyvinyl acetate fibers; polyurethane foams and mixtures thereof. These and other suitable fibers and the nonwoven materials prepared therefrom are generally described in Riedel, "Nonwoven Bonding Methods and Materials," Nonwoven World (1987); The Encyclopedia Americana, vol. 11, pp. 147–153, and vol. 26, pp. 566–581 (1984); U.S. Pat. No. 4,891,227, to Thaman et al., issued Jan. 2, 1990; and U.S. Pat. No. 4,891,228 which are all incorporated by reference herein in their entirety.)

The substrate employed in the present invention is formed from hydroentangled fibers. One way to prepare a substrate from hydroentangled fibers is to position a web of fibers on a topographical support member comprising an essentially planar background surface with at least one recessed region significantly displaced from the background surface of the forming plate. Typically, the support member comprises a multiplicity of recessed regions, positioned as depressions is some predetermined array, that will form a desired pattern of raised portions on the nonwoven substrate. The fibrous web is presoaked or wetted out with water while on this support member to ensure that as it is treated it will remain on the support member. The support member with the fibrous web thereon is passed under a series of orifices from each of which a fluid, such as water, is ejected under high pressure and directed toward the upper surface of the fibrous web, i.e., that surface of the web which is out of contact with the topographical support member. Initially, these fluid forces "mold" the starting web to the three dimensional support member; as the process of applying fluid force continues, the fibers are entangled and locked together so as to provide a nonwoven substrate comprising a base surface and one or more discrete, raised fibrous regions which are permanently positioned with respect to one another. The water is then transported away from the support member, preferably using a vacuum. The fibrous web is de-watered. The de-watered formed substrate is removed from the support member. The formed substrate is passed over a series of drying drums to dry the substrate. The substrate can then be finished or otherwise processed as desired. Processes for preparing hydroentangled webs are well known in the art. See, for example, Evans; U.S. Pat. No. 3,485,786; issued Dec. 23, 1969; Kalwarres; U.S. Pat. No. 2,862,251 and Griswold; U.S. Pat. No. 3,025,585, all of which describe hydroentangling procedures generally and all of which are herein incorporated by reference. See also U.S. Pat. No. 5,674,591; James et al; issued Oct. 7, 1997 which specifically describes a hydroentangling process, including the apparatus used in said process, which can be used to prepare the patterned substrates employed in the present invention. U.S. Pat. No. 5,674,591 is incorporated herein in its entirety.

The substrates of the present invention are preferably single layer substrates. By "single layer" is meant that the substrate is removed from the topographical support layer as a single, unitary piece, and does not require the addition of other fibrous or nonfibrous structural components. In particular, a scrim is not joined to the nonwoven substrate employed in the present invention. It is understood that the single layer substrates herein can include one or more fiber types, including different synthetic fibers, different natural fibers, and/or a combination of synthetic and natural fibers. Such different fibers can be blended in a homogenous manner through the thickness of the substrate, or alternatively, can be arranged in strata through the thickness of the substrate.

As hereinbefore described, the particular nonwoven, hydroentangled substrates of the present invention comprise a base surface having on a substantial portion of the base surface a three-dimensional pattern comprising a plurality of discrete, raised fibrous regions.

In one embodiment of the present invention, the basis weight and the density, respectively, of the raised fibrous regions are substantially the same as the basis weight and density, respectively, of the base surface. As used herein, the term "basis weight" is the weight of a unit area of fibrous web or portion thereof being characterized. As used herein, the term "density" is the weight of a unit volume of a fibrous web or portion thereof being characterized. Traditional embossing patterning processes produce regions of varying density.

In a second embodiment of the present invention, the basis weight of the raised fibrous portions is greater than the basis weight of the base surface and the density of the raised fibrous regions are substantially the same as the density of the base surface. In a third embodiment of the present invention, the basis weight of some of the raised fibrous regions are substantially the same as the basis weight of the base surface and the basis weight of other raised fibrous regions are greater than the basis weight of the base surface. In this embodiment, as in the other embodiments, the density of all of the raised fibrous areas is essentially the same as the density of the base surface.

The raised fibrous regions of the substrate herein are joined to the base surface of the substrate herein by a fibrous transition region. The fibrous transition region comprises a fiber-poor region and a fiber-rich region. The fibrous transition region, including both the fiber region and fiber-rich region are described in detail in U.S. Pat. No. 5,674,591, herein incorporated in its entirety by reference.

The average basis weight of the nonwoven, patterned substrates used in the present invention ranges from about 40 to about 90 grams per square meter, preferably from about 40 to about 75 grams per square meter, more preferably from about 50 to about 65 grams per square meter as measured by INDA Standard Test IST 130.1. The caliper of the substrates employed in the present invention ranges from about 0.3 to about 1.05 mm, preferably from about 0.5 to about 1.00 mm, more preferably from about 0.6 to about 0.9 mm, as measured by INDA Standard Test IST 120.1 (95).

The substrates of the present invention can be, but are not necessarily, appertured.

B. The Aqueous Liquid Cleansing Composition

1. The Cleansing Surfactant

The personal cleansing wipes articles of the present invention comprise an effective amount of a cleansing surfactant to provide a cleansing benefit. Typically, the aqueous cleansing composition used in the present invention comprises from about 0.5% to about 12.5%, preferably from about 0.75% to about 11%, and more preferably from about 1% to about 10%, and most preferably from about 1% to about 5%, based on the weight of the cleansing composition, of a cleansing surfactant. Preferably, these surfactants or combinations of surfactants should be mild, which means that these surfactants provide sufficient cleansing or detersive benefits but do not overly dry the skin.

A wide variety of cleansing surfactants are useful herein and include those selected from the group consisting of anionic surfactants, nonionic surfactants, amphoteric surfactants, cationic surfactants, and mixtures thereof.

a. Anionic Surfactants

Nonlimiting examples of anionic surfactants useful in the compositions of the present invention are disclosed in McCutcheon's, *Detereents and Emulsifiers,* North American edition (1986), published by allured Publishing Corporation; McCutcheon's, *Functional Materials,* North American Edition (1992); and U.S. Pat. No. 3,929,678, to Laughlin et al., issued Dec. 30, 1975 all of which are incorporated by reference herein in their entirety.

A wide variety of anionic surfactants are useful herein. Nonlimiting examples of anionic surfactants include those selected from the group consisting of sarcosinates, sulfates, isethionates, taurates, phosphates and mixtures thereof. Amongst the isethionates, the alkoyl isethionates are preferred, and amongst the sulfates, the alkyl and alkyl ether sulfates are preferred. The alkoyl isethionates typically have the formula $RCO-OCH_2CH_2SO_3M$ wherein R is alkyl or alkenyl of from about 10 to about 30 carbon atoms, and M is a watersoluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, and mixtures thereof.

The alkyl and alkyl ether sulfates typically have the respective formulae $ROSO_3M$ and $RO(C_2H_4O)~SO_3M$, wherein R is alkyl or alkenyl of from about 10 to about 30 carbon atoms, x is from about 1 to about 10, and M is a water-wluble cation such as ammonium, sodium, potassium and triethanolamine. Another suitable class of anionic surfactants are the water-soluble salts of the organic, sulfuric acid reaction products of the general formula:

$$R_1\text{---}SO_3\text{---}M$$

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials include the sarcosinates, nonlimiting examples of which include sodium lauroyl sarcosinate, sodium cocoyl sarcosinate, and anunonium lauroyl sarcosinate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animnal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Other anionic materials include phosphates such as monoalkyl, dialkyl, and trialkylphosphate salts.

Other anionic materials include alkanoyl sancosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Also useful are taurates which are based on taurine, which is also known as 2-aminoethanesulfonic acid. Examples of taurates include N-alkyltaurines such as the one prepared by reacting dodecylamine with sodium isethionate according to the teaching of U.S. Pat. No. 2,658,072 which is incorporated herein by reference in its entirety.

Nonlimiting examples of preferred anionic surfactants useful herein include those selected from the group consisting of sodium lauryl sulfate, anmmonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl sarcosinate, and mixtures thereof.

Especially preferred for use herein are anmnonium lauryl sulfate and anmonium laureth sulfate.

b. Nonionic Surfactants

Nonlimiting examples of nonionic surfactints for use in the compositions of the present invention are disclosed in McCutcheon's, *Detergents and Emulsifiers,* North American edition (1986), published by allured Publishing Corporation; and McCutcheon's, *Functional Materials,* North Amnerican Edition (1992); both of which are incorporated by reference herein in their entirety.

Nonionic surfactants useful herein include those selected from the group consisting of polyoxyethylenes, alkyl glucosides, alkyl polyglucosides, polyhydroxy fatty acid amides, alkoxylated fatty acid esters, sucrose esters, amine oxides, and mixtures thereof.

Alkyl glucosides and alkyl polyglucosides are useful herein, and can be broadly defined as condensation products of long chain alcohols, e.g. C8–30 alcohols, with sugars or starches or sugar or starch polymers. i.e., glycosides or polyglycosides. These compounds can be represented by the formula $(S)_n$—O—R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylaled derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. No. 2,703,798, to A. M. Schwartt, issued Mar. 8, 1955; and U.S. Pat. No. 1,985,424, to Piggott, issued Dec. 25, 1934; which are incorporated herein by reference in their entirety.

Other examples of nonionic surfactants include amine oxides. Amine oxides correspond to the general formula $R_1R_2R_3NO$, wherein $R_1$ contains an alkyl, alkenyl or monobydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or bydroxypropyl radicals. The arrow in the formula is a conventional representation of a semipolar bond. Examples of amine oxides suitable for use in this invention include dimethyl-dodecylamine oxide, oleyidi(2-hydroxyethyl) amine oxide, dimethyloctylamine oxide, dimethyl-decylamine oxide, dimethyl-tetradecylamine oxide, 3,6,9-trioxaheptadecyidiethylamine oxide, di(2-hydroxyethyl)-tetradecylamine oxide, 2-dodecoxyethyidimethylamine oxide, 3-dodecoxy-2-hydroxypropyidi(3-hydroxypropyl) amine oxide, dimethylhexadecylaamine oxide.

Nonlimiting examples of preferred nonionic surfactants for use herein are those selected form the group consisting of polyoxyethylenes, C8–C14 glucose amides, C8–C14 alkyl polyglucosides, sucrose cocoate, sucrose laurate, lauramine oxide, cocoamine oxide, and mixtures thereof.

c. Aimghoteric Surfactants

The term "amphoteric surfactant," as used herein, is also intended to encompass zwitterionic surfactants, which are well known to formulators skilled in the art as a subset of amphoteric surfactants.

A wide variety of amphoteric surfactants can be used in the compositions of the present invention. Particularly useful are those which are broadly described as derivatives of aliphatic secondary and tertiary amidines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, *Detergents and Emulsifiers,* North American edition (1986), published by allured Publishing Corporation; and McCutcheon's, *Functional Materials,* North American Edition (1992); both of which are incorporated by reference herein in their entirety.

Nonlimiting examples of amphoteric or zwitterionic surfactants are those selected from the group consisting of betaines, sultaines, hydroxysultaines, alkyliminoacetates, iminodialkanoatea, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphboxyethyl betaine, cetyl dimethyl carboxymethyl betaine, cetyl dimethyl betaine (available as Lonizaine 16SP from Lonza Corp.), lauryl bis-(2-hydroxyethyl) cabbozymethyl betaine, oleyl dimethyl gamma-carboxypropyl betaine, lauryl bis-(2-hydroxypropyl)alpharboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the RCONH(CH$_2$)$_3$ radical is attached to the nitrogen atom of the betaine), oleyl betaine (available as amphoteric Velvetex OLB-50 from Henkel), and coeamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

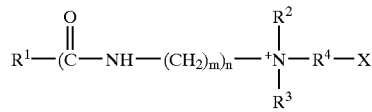

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected from the group consisting of $CO_2$, $SO_3$ and $SO_4$; $R^4$ is selected from the group consisting of saturated or unsaturated, straight or branched chain alkyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine)

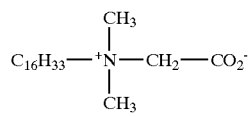

Cocamidopropylbetaine

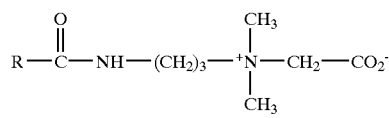

wherein R has from about 9 to about 13 carbon atoms

Cocamidopropyl hydroxy sultaine

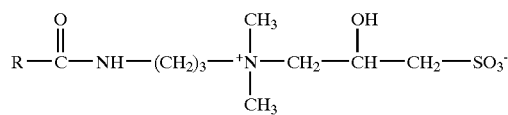

wherein R has from about 9 to about 13 carbon atoms,

Examples of other useful amphoteric surfactants are alkyliminoacetates, and iminodialkanoates and arninoalkanoates of the formulas RN[CH$_2$)$_m$CO$_2$M]$_2$ and RNH(CH$_2$)$_m$ CO$_2$M wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3dodecyl-aminopropionate, sodium 3-dodecylaminopropane sulfonate, N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include amphoteric phosphates, such as coamidopropyl PG-ditwonium chloride phosphate (commercially available as Monaquat NTC, from Mona Corp.). Also useful are amphoacetates such as disodium lauroamphodiacetate, sodium lauroamphoacetate, and mixtures thereof.

d. Cationic Surfactants

Nonlimiting examples of cationic surfactants useful herein are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonlimiting examples of cationic surfactants useful herein include cationic alkyl ammonium salts such as those having the formula:

$$R_1R_2R_3R_4N^+X^-$$

wherein $R_1$, is selected from an alkyl group having from about 12 to about 18 carbon atoms, or aromatic, aryl or alkaryl groups having from about 12 to about 18 carbon atoms; $R_1$, $R_3$, and $R_4$ are independently selected from hydrogen, an alkyl group having from about 1 to about 18 carbon atoms, or aromatic, aryl or alkaryl groups having from about 12 to about 18 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 18 carbon atoms; $R_2$ is selected from H or an alkyl group having from about 1 to about 18 carbon atoms; $R_3$ and $R_4$ are independently selected from H or an alkyl group having from about 1 to about 3 carbon atoms; and X is as described in the previous paragraph.

Most preferably, $R_1$ is an alkyl group having from about 12 to about 18 carbon atoms; $R_2$, $R_3$, and $R_4$ are selected from H or an alkyl group having from about 1 to about 3 carbon atoms; and X is as described previously.

Alternatively, other useful cationic surfactants include amino-amides, wherein in the above structure $R_1$ is alternatively $R_5CO$—$(CH_2)_n$—, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl anunonium chloride, lauryl trimethyl ammonium bromide, stearyl trimethyl ammonium chloride, stearyl trimethyl ammonium bromide, lauryl dimethyl ammonium chloride, stearyl dimethyl cetyl disallow dimethyl ammonium chloride, dicetyl ammonium chloride, dicetyl ammonium bromide, dilauryl anunonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include disallow dimethyl ammonium chloride, disallow dimethyl ammonium methyl sulfate, di(hydrogenated tallow) dimethyl ammonium chloride, di(hydrogenated tallow) dimethyl ammonium acetate, disallow dipropyl ammonium phosphate, disallow dimethyl ammonium nitrate, di(coconutalkyl)dimethyl anmmonium chloride, di(coconutalkyl)dimethyl anmmonium bromide, tallow ammonium chloride, coconut ammonium chloride, stearamnidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamnidopropyl dimethyl ammonium lactate, and mixtures thereof.

Preferred cationic surfactants useful herein include those selected from the group consisting of dilauryl dimethyl anmnonium chloride, distearyl dimethyl ammonium chloride, dimyristyl dimethyl ammonium chloride, dipalmityl dimethyl ammonium chloride, distearyl dimethyl ammonium chloride, and mixtures thereof.

2. Optional Ingredients a. Conditioning Ingredients

The aqueous cleansing composition used in the personal cleansing wipes of the present invention can optionally and preferably comprise an lipophilic skin conditioning agent which is useful for providing a conditioning benefit to the skin during the use of the product. The aqueous cleansing solution employed in the present invention typically comprises from about 0.1% to about 30%, preferably from about 0.5% to about 20%, preferably from about 1% to about 10%, and more preferably from about 1% to about 5% by weight of the aqueous cleansing composition.

The lipophilic skin conditioning agent is selected from one or more oil soluble conditioning agents such that the weighted arithmetic mean solubility parameter of the lipophilic skin conditioning agent is less than or equal to 10.5. It is recognized, based on this mathematical definition of solubility parameters, that it is possible, for example, to achieve the required weighted arithmetic mean solubility parameter, i.e. less than or equal to 10.5, for alipophilic skin conditioning agent comprising two or more compounds if one of the compounds has an individual solubility parameter greater than 10.5.

Solubility parameters are well known to the formulation chemist of ordinary skill in the art and are routinely used as a guide for determining compatibility's and solubilities of materials in the formulation process.

The solubility parameter of a chemical compound, 5, is defined as the square root of the cohesive energy density for that compound. Typically, a solubility parameter for a compound is calculated from tabulated values of the additive group contributions for the beat of vaporization and molar volume of the components of that compound, using the following equation:

$$\delta = \left[\frac{\sum_i E_i}{\sum_i m_i}\right]^{1/2}$$

wherein $\Sigma_i E_i$=the sum of the heat of vaporization additive group contributions, and $\Sigma_i\ m_i$=the sum of the molar volume additive group contributions Standard tabulations of heat of vaporization and molar volume additive group contributions for a wide variety of atoms and groups of atoms are collected in Barton, A.F.M. *Handbook of Solubility Parameters*, CRC Press, Chapter 6, Table 3, pp. 64–66 (1985), which is incorporated by reference herein in its entirety. The above solubility parameter equation is described in Fedors, R. F., "A Method for Estimating Both the Solubility Parameters and Molar Volumes of Liquids", Polymer *Engineering and Science*, vol. 14, no. 2, pp. 147–154 (February 1974), which is incorporated by reference herein in its entirety.

Solubility parameters obey the law of mixtures such that the solubility parameter for a mixture of materials is given by the weighted arithmetic mean (i.e. the weighted average) of the solubility parameters for each component of that mixture. See, *Handbook of Chemistry and Physics*, 57th edition, CRC Press, p. C-726 (1976–1977), which is incorporated by reference herein in its entirety.

Formulation chemists typically report and use solubility parameters in units of cal/cm$^3$)$^{1/2}$. The tabulated values of additive group contributions for heat of vaporization in the *Handbook of Solubility Parameters* arm reported in units of kJ/mol. However, these tabulated bed of vaporization values are readily converted to cal/mol using the following well-known relationships:

1 J/mol=0.239006 cal/mol and 1000 J=1 kJ.

See Gordon, A. J. et al., *The Chemist's Companion*, John Wiley & Sons, pp. 456–463, (1972), which is incorporated by reference herein in its entirety.

Solubility parameters have also been tabulated for a wide variety of chemical materials. Tabulations of solubility parameters are found in the above-cited *Handbook of Solubility Parameters*. Also, see "Solubility Effects In Product, Package, Penetration, And Preservation", C. D. Vaughan, *Cosmetics and Toiletries*, vol. 103, October 1988, pp. 47–49, which is incorporated by reference herein in its entirety.

Nonlimiting examples of lipophilic skin conditioning agents useful herein include those selected from the group consisting of mineral oil, petroleum, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol C4–C20 alkyl ethers, di C8–C30 alkyl ethers, and mixtures thereof.

Mineral oil, which is also known as petroleum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415–417 (1993), which are incorporated by reference herein in their entirety.

Petroleum, which is also known as petroleum jelly, is a colloidal system of nonstraight-chain solid hydrocarbons and high-boiling liquid hydrocarbons, in which most of the liquid hydrocarbons arm held inside the micelles. See The Merck Index, Tenth Edition, Entry 7047, p. 1033 (1983); Schindler, *Drug. Cosmet. Ind.*, 89, 36–37, 76, 78–80, 82 (1961); and International Cosmetic Ingredient Dictionary, Fifth Edition, vol. 1, p. 537 (1993),which are incorporated by reference herein in their entirety.

Straight and branched chain hydrocarbons having from about 7 to about 40 carbon atoms are useful herein. Nonlimiting examples of these hydrocarbon materials include dodecane, isododocane, squalane, cholesterol, hydrogenated polyisobutylene, docosane (i.e. a $C_{22}$ hydrocarbon), hexadecane, isohexadecane (a commercially available hydrocarbon sold as Permethyl ® 101A by Presperse, South Plainfield, N.J.). Also useful are the C7–C40 isoparaffins, which are C7–C40 branched hydrocarbons.

Also useful are C1–C30 alcohol esters of C1–C30 carboxylic acids and of C2–C30 dicarboxylic acids, including straight and branched chain materials as well as aromatic derivatives.

Also useful are esters such as monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2ethylhexyl palmitate, isodecyl neopentanoate, di-2ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, caprilic/capric triglyceride, PEG-6 caprylic/capric triglyceride, PEG-8 caprylic/capric triglyceride, and mixtures thereof.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoleate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates-:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. No. 2,831,854, U.S. Pat. No. 4,005,196, to Jandacek, issued Jan. 25, 1977; U.S. Pat. No. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued April 26, 1994; U.S. Pat. No. 5,305,514, to Letton et al., is Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Nonvolatile silicones such as polydialkylsiloxanes, polydiarylsiloxanes, and polyalkarylsiloxanes are also useful oils. These silicones are disclosed in U.S. Pat. No. 5,069,897, to Orr, issued Dec. 3, 1991, which is incorporated by reference herein in its entirety. The polyalkylsiloxanes correspond to the general chemical formula $R_3SiO[R_2SiO]_xSiR_3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, nonliniting examples of which include the Vicasil® series sold by General Electric Company and the Dow Corning® 200 series sold by Dow Corning Corporation. Specific examples of polydimethylsiloxanes useful herein include Dow Coming® 225 fluid having a viscosity of 10 centistokes and a boiling point greater than 200° C., and Dow Coming® 200 fluids having viscosities of 50, 350, and 12,500 centistokes, respectively, and boiling points greater than 200° C. Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Coming® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Vegetable oils and hydrogenated vegetable oils are also useful herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are C4–C20 alkyl ethers of polypropylene glycols, C1–C20 carboxylic acid esters of polypropylene glycols, and di–C8–C30 alkyl ethers. Nonlimiting examples of these materials include PPG-14 butyl ether, PPG-15 stearyl ether, dioctyl ether, dodecyl octyl ether, and mixtures thereof.

b. Active Ingredients

The personal cleansing wipes of the present invention can also optionally comprise a safe and effective amount of one or more active ingredients or pharmaceutically-acceptable salts thereof.

The term "safe and effective amount" as used herein, means an amount of an active ingredient high enough to modify the condition to be treated or to deliver the desired skin benefit, but low enough to avoid serious side effects, at a reasonable benefit to risk ratio within the scope of sound medical judgment. What is a safe and effective amount of the active ingredient will vary with the specific active, the ability of the active to penetrate through the skin, the age, health condition, and skin condition of the user, and other like factors.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are sot intended to limit the active ingredient to that particular application or applications listed. Also, pharmaceutically-acceptable salts of these active ingredients are useful herein. The following active ingredients are useful in the compositions of the present invention.

Anti-Acne Actives: Examples of useful anti-acne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives: Examples of antiwrinkle and anti-skin atrophy actives include retinoic acid and its derivatives (e.g., cis and trans); retinol; retinyl esters; niacinamide, salicylic acid and derivatives thereof; sulfur-containing D and L amino acids and their derivatives and salts, particularly the N-acetyl derivatives, a preferred example of which is N-acetyl-L-cysteine; thiols, e.g. ethane thiol; hydroxy acids, phytic acid, lipoic acid; lysophosphatidic acid, and skin peel agents (e.g., phenol and the like).

Non-Steroidal Anti-Inflammatory Actives (NSAIDS): Examples of NSAIDS include the following categories: propionic acid derivatives; acetic acid derivatives; fenamic acid derivatives; biphenylcarboxylic acid derivatives, and oxicams. All of these NSAIDS are filly described in U.S. Pat. No. 4,985,459 to Sunshine et al., issued Jan. 15, 1991, incorporated by reference herein in its entirety. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics: Examples of topical anesthetic drugs include benzocaine, lidocaine, bupivacaine, chlorprocaine, dibucaine, etidocaine, nepivacaine, tetracaine, dyclonine, hexylcaine, procaine, cocaine, ketamine, pramoxine, phenol, and pharmaceutically acceptable salts thereof.

Artificial Tanning Agents and Accelerators. Examples of artificial tanning agents and accelerators include dihydroxyacetaone, tyrosine, tyrosine esters such as ethyl tyrosinate, and phospbo-DOPA.

Antimicrobial and Antifungal Actives: Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione and clotrimazole.

Preferred examples of actives useful herein include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'trichlorocarbanilide, octopirox, lidocaine hydrochloride, clotrimazole, miconazole, neocycin sulfate, and mixtures thereof.

Sunscreen Actives: Also useful herein are sunscreening actives. A wide variety of sunscreening agents are described in U.S. Pat. No. 5,087,445, to Haffey et al., issued February 11, 1992; U.S. Pat. No. 5,073,372, to Turner et al., issued December 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued June 26, 1990; and U.S. Pat. No. 4,999,186, to Sabatelli et al., issued Mar. 12, 1991; these two references are incorporated by reference herein in their entirety. Especially preferred examples of these sunscreens include those selected from the group consisting of 4-N,N-(2ethylhexyl) methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl)-methylaminobenzoic acid ester of 2-hydroxy442-hydroxyethoxy)benzophenone, 4-N,N-(2-ethylhexyl)-methylaminobenzoic acid ester of 4-(2-hydroxyethoxy) dibenzoylmethane, and mixtures thereof. Exact amounts of sunscreens which can be employed will vary depending upon the sunscreen chosen and the desired Sun Protection Factor (SPF) to be achieved. SPF is a commonly used measure of photoprotection of a sunscreen against erythema. See *Federal Register*, Vol. 43, No. 166, pp. 38206–38269, Aug. 25, 1978, which is incorporated herein by reference in its entirety.

Nonlimiting examples of preferred actives useful herein include those selected from the group consisting of salicylic acid, benzoyl peroxide, niacinamide, cis-retinoic acid, trans-retinoic acid, retinol, retinyl palmitate, phytic acid, N-acetyl L-cysteine, azelaic acid, lipoic acid, resorcinol, lactic acid, glycolic acid, ibuprofen, naproxen, hydrocortisone, phenoxyethanol, phenoxypropanol, phenoxyisopropanol, 2,4,4,'-trichloro-2'-hydroxy diphenyl ether, 3,4,4'-trichlorocarbanilide, 2-ethylhexyl p-methoxycinnamic acid, oxybenzone, 2-phenylbenzimidozole-5-sulfonic acid, dihydroxyacetone, and mixtures thereof.

C. Proton Donating Agents

The aqueous cleansing composition comprising the personal cleansing wipes of the present invention can optionally comprise from about 0.1% to about 10%, preferably from about 0.5% to about 8%, more preferably from about 1% to about 5%, based on the weight of the cleansing composition, of a proton donating agent. By "proton donating agent" it is meant any acid compound or mixture thereof, which results in undissociated acid on the skin after use. Proton donating agents can be organic acids, including polymeric acids, mineral acids or mixtures thereof.

A nonexclusive list of examples of organic acids which can be used as the proton donating agent are adipic acid, tartaric acid, citric acid, maleic acid, malic acid, succinic acid, glycolic acid, glutaric acid, benzoic acid, malonic acid, salicylic acid, gluconic acid, polymeric acids, their salts, and mixtures thereof A non-exclusive list of examples of mineral acid for use herein are hydrochloric, phosphoric, sulfuric and mixtures thereof.

Polymeric acids are especially preferred acids for use herein from the standpoint that they cause less stinging to the skin than other acids. As used herein, the term "polymeric acid" refers to an acid with repeating units of carboxylic acid groups joined together into one chain. Suitable polymeric acids can include homopolymers, copolymers and terpolymers, but must contain at least 30 mole % carboxylic acid groups. Specific examples of suitable polymeric acids useful herein include straight-chain poly(acrylic) acid and its copolymers, both ionic and nonionic, (e.g., maleic-acrylic, sulfonic-acrylic, and styrene-acrylic copolymers), those cross-linked polyacrylic acids having a molecular weight of less than about 250,000, preferably less than about 100,000 poly ($\alpha$-hydroxy) acids, poly (methacrylic) acid, and naturally occurring polymeric acids such as carageenic acid, carboxy methyl cellulose, and alginic acid. Straight-chain poly(acrylic) acids are especially preferred for use herein.

In one preferred embodiment of the present invention, the proton donating agent is used to buffer the pH of the aqueous cleansing composition to a pH ranging from about 3.0 to about 6.0, more preferably from about 3.0 to about 5.0 and most preferably from about 3.5 to about 4.5.

d. Water Soluble Conditioning Agents

The present invention can also optionally comprise water soluble conditioning agents. Such water soluble conditioning agents are typically included in the aqueous cleansing composition employed herein t a level ranging from about 0.1% to about 2%, preferably from about 0.2% to about 1.5%, more preferably from about 0.5% to about 1% by weight of the aqueous cleansing composition.

Nonlimiting examples of conditioning agents useful as water soluble conditioning agents include those selected from the group consisting of polyhydric alcohols, polypropylene glycols, polyethylene glycols, ureas, pyrolidone carboxylic acids, ethoxylated and/or propoxylated C3–C6 diols and triols, alphahydroxy C2–C6 carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful water soluble conditioning agents include materials such as urea; guanidine; glycolic acid and glycolate salts (e.g. ammonium and quaternary alkyl ammonium); lactic acid and lactate salts (e.g. ammonium and quaternary alkyl anmmonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; and mixtures thereof. Also useful are materials such as aloe vera in any of its variety of forms (e.g., aloe vera gel), chitin, starch-grafted sodium polyacrylates such as Sanwet (RTM) IM-1000, IM-1500, and IM-2500 (available from Celanese Superabsorbent Materials, Portsmouth, Va.); lactamide monoethanolamine; acetamide monoethanolamine; and mixtures thereof. Also useful are propoxylated glycerols as described in propoxylated glycerols described in U.S. Pat. No. 4,976,953, to Orr et al., issued Dec. 11, 1990, which is incorporated by reference herein in its entirety.

e. Drying Agents

Drying agents can be employed in the aqueous cleansing compositions employed herein to boost the drying rate of the liquid composition once it applied to the skin via rubbing the wipe product on the skin. Some aqueous cleansing compositions can give a sticky impression when they are applied to the skin, especially during the time it takes for the composition to dry. It has been found that fast-drying compositions provide a softer, smoother skin feel, with less stickiness. Suitable drying agents include isoparaffin, alcohols and combinations thereof. A mixture of isoparaffin and ethanol is especially preferred. Drying agents are typically included in the cleansing compositions employed herein at a level ranging from about 1% to about 60%, preferably from about 3% to about 40%, more preferably from about 5% to about 20% by weight.

f. Other Optional Ingredients

The compositions of the present invention can comprise a wide range of other optional components. These additional components should be pharmaceutically acceptable. The *CTFA Cosmetic Ingredient Handbook,* Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these and other functional classes include: abrasives, absorbents, anticaking agents, antioxidants, vitamins, binders, biological additives, buffering agents, bulking agents, chelating agents, chemical additives, colorants, cosmetic astringents, cosmetic biocides, denaturants, drug astringents, external analgesics, film formers, flagrance components, humectants, opacifying agents, pH adjusters, preservatives, propellants, reducing agents, skin bleaching agents, and sunscreening agents.

Also useful herein arm aesthetic components such as fragrances, pigments, colorings, essential oils, skin sensates, astringents, skin soothing agents, and skin healing agents.

g. Viscosity of Aqueous Cleansing Composition

The aqueous cleansing compositions employed in the wipes product herein preferably have a viscosity in the range of from about 1 to about 1000, preferably from about 5 to about 200 centipoise as measured by a Brookfield Digital Viscometer, Model DV-II+ Version 3.2 according to the operating instructions set forth in Manual No. M/92-161-H895.

Examples of suitable aqueous cleansing compositions for use herein are set forth in the following U.S. Patents and U.S. Patent Applications, all of which are herein incorporated by reference: U.S. patent application Ser. No. 08/727, 807 pages 3–6 and 8); U.S. patent application Ser. No. 08/868,668 filed on Jun. 4, 1997; U.S. Pat. No. 4,941,995 issued Jul. 17, 1990 to Richards et al; U.S. Pat. No. 4,904, 524 issued Feb. 27, 1990 to Yoh; U.S. Pat. No. 5,043,155 to Puchalski; U.S. Pat. No. 5,534,265 to Fowler; U.S. Pat. No. 5,648,083 to Blieszer et al.; and U.S. patent application Ser. No. 08/736,471 filed Oct. 24, 1996.

II. Preparation of Absorbent Sheets Impregnated with Aqueous Liquid Cleansing Solution Any method suitable for the application of aqueous or aqueous/alcoholic impregnates, including flood coating, spray coating or metered dosing, can be used to impregnate the substrates herein with the emulsion composition described herein. More specialized techniques, such as Meyer Rod, floating knife or doctor blade, which are typically used to impregnate cleansing solutions into absorbent sheets may also be used.

The cleansing solution should preferably comprise from about 100% to about 400%, preferably from about 200% to about 400% by weight of the absorbent sheet.

Prior to or after impregnation of the liquid cleansing solution into the substrate, the substrate may be folded into stacks. The substrate is then typically packaged in any of the moisture and vapor impermeable packages known in the art.

EXAMPLES

The following are nonlimiting examples of the personal cleansing wipes compositions of the present invention.

Aqueous Cleansing Compositions

| Ingredient | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| lipophilic skin conditioner | 1.00 | — | 1.84 | 1.84 | 1.84 | 1.84 | 0.67 | 1.84 | 1.84 | 1.00 |
| thickener | — | — | 0.75 | 0.75 | 0.75 | 0.75 | — | 1.80 | 1.80 | — |
| nonionic surfactant | 0.30 | — | 1.00 | 1.00 | 1.00 | 1.00 | — | 0.50 | 0.50 | 1.00 |
| ammonium lauryl sulfate | 0.60 | 0.60 | 0.60 | 0.60 | 0.60 | 0.60 | 0.60 | 0.60 | 0.60 | — |
| triclosan | 0.15 | 0.15 | 0.15 | 0.15 | 0.15 | 0.15 | 0.15 | 0.15 | — | 0.15 |
| isoparaffin | — | — | — | — | — | 1.50 | — | 1.50 | 1.50 | — |
| ethyl alcohol | — | 10.00 | 10.00 | 10.00 | — | 10.00 | 10.00 | 10.00 | 10.00 | — |
| organic acid | 2.50 | 2.5 | 2.5 | 1.00 | 1.00 | 2.50 | 2.50 | 1.00 | 1.00 | — |
| minor ingredients | 3.36 | 1.32 | 0.32 | 0.32 | 0.32 | 0.32 | 0.30 | 0.32 | 0.32 | 1.36 |
| water | QS | QS | QS | QS | QS | QS | QS | QS | QS | QS |
| viscosity (cp) | 1–5 | 1–5 | 10–20 | 10–20 | 10–20 | 10–20 | 10–20 | 10–20 | 10–20 | <500 |
| pH | 3.7 | 3.7 | 3.7 | 3.7 | .37. | 3.7 | 3.7 | 3.7 | 3.7 | — |

The aqueous cleansing compositions (Examples 1–10) are each impregnated onto substrates of the type described in Examples 1 and 2 of U.S. Pat. No. 5,674, 591 wherein the basis weight of the substrate is 60 grams per square meter and wherein the pattern is a starburst. 230% by weight of the substrate of the aqueous cleansing composition is impregnated into the substrate by pouring the compositions onto the substrate via a cup. Each of the resulting wipes articles will exhibit desirable softness, feel and cleansing properties.

The aqueous cleansing compositions (Examples 1–10) are each impregnated onto substrates of the type described in Examples1 and 2 of U.S. Pat. No. 5,674, 591 wherein the basis weight of the substrate is 60 grams per square meter and wherein the pattern is a zigzag. 230% by weight of the substrate of the aqueous cleansing composition is impregnated into the substrate by pouring the compositions onto the substrate via a cup. Each of the resulting wipes articles will exhibit desirable softness, feel and cleansing properties.

What is claimed is:

1. A personal cleansing wipe article having superior softness feel and cleansing properties, which wipe article comprises:
    A. a single layer, non-embossed, nonwoven substrate having an average basis weight ranging from about 40 to about 90 grams per square meter, having a caliper ranging from about 0.3 to about 1.05 millimeters, formed from hydroentangled fibers, said substrate having on a substantial portion of a base surface thereof a three-dimensional pattern, which pattern comprises a plurality of discrete, raised fibrous regions, wherein the raised fibrous regions have a density which is substantially the same as the density of the base surface, and wherein said raised fibrous regions are joined to said base surface by a fibrous transition region; and
    B. an aqueous liquid cleansing composition comprising
        a. from about 0.5% to about 12.5% of the cleansing surfactant;
        b. from about 0.5% to about 5% of a lipophilic skin moisturizing agent wherein the cleansing surfactant comprises at least one anionic surfactant, and wherein said aqueous liquid cleansing composition is coated onto or impregnated into said substrate to the extent of from about 100% to about 400% by weight of the substrate; and
        c. from about 1% to about 6% of a drying agent.

2. A personal cleansing wipe article according to claim 1 wherein said raised fibrous regions have a basis weight which is substantially the same as the basis weight of the base surface.

3. A personal cleansing wipe article according to claim 1 wherein the basis weight of the raised fibrous regions and is greater than the basis weight of the base surface.

4. A personal cleansing wipe article according to claim 1 wherein the basis weight of some of the raised fibrous regions is substantially the same as the basis weight of the base surface ad wherein the basis weight of the remainder of the raised fibrous regions is greater than the basis weight of the base surface.

5. A personal cleansing wipe article according to claim 1 wherein the drying agent comprises isoparaffin.

6. A personal cleansing wipe article according to claim 1, wherein the cleansing composition comprises from about 0.5% to about 5% of the cleansing surfactant.

7. A personal cleansing wipe article according to claim 1, wherein the cleansing composition comprises from about 0.5% to about 5% of the anionic surfactant.

8. A process for preparing the personal cleansing wipe article having superior softness, feel and cleansing properties according to claim 1, which process comprises:
    A. placing a web of fibers on a foraminous forming plate or topographical support member comprising an essentially planar background surface with at least one recessed region significantly displaced from the background surface of the forming plate;

B. applying fluid force to the upper surface of the fibrous web such that the fibers become entangled and a patterned substrate is formed;

C. transporting the fluid away from the patterned substrate; and

D. coating or impregnating the patterned substrate with an aqueous cleansing composition comprising a. from about 0.5% to about 12.5% of the cleansing surfactant; and b. from about 0.5% to about 5% of a lipophilic skin moisturizing agent to the extent of from about 100% to about 400% by weight of the substrate, wherein the cleansing surfactant comprises at least one anionic surfactant.

* * * * *

UNITED STATES PATENT AND TRADEMARK OFFICE
CERTIFICATE OF CORRECTION

PATENT NO.  : 6,753,063 B1
DATED       : June 22, 2004
INVENTOR(S) : D. J. Pung et al.

It is certified that error appears in the above-identified patent and that said Letters Patent is hereby corrected as shown below:

Column 1,
Line 55, "arm" should read -- are --.
Line 56, "cleaning" should read -- cleansing --.

Column 2,
Line 51, "amel" should read -- arnel --.
Line 52, "66." should read -- 66, --.

Column 4,
Line 51, "*Detereents*" should read -- *Detergents* --.
Line 66, "watersoluble" should read -- water soluble --.

Column 5,
Line 9, "water-wluble" should read -- water-soluble --.
Line 26, "anunonium" should read -- ammonium --.
Line 33, "animnal" should read -- animal --.
Line 40, "sancosinates" should read -- sarcosinates --.
Line 55, "anmmonium" should read -- ammonium --.
Line 61, "anmnonium" should read -- ammonium --.
Line 62, "anmonium" should read -- ammonium --.
Line 64, "surfactints" should read -- surfactants --.

Column 6,
Line 1, "Amnerican" should read -- American --.
Line 13, "polymers." should read -- polymers, --.
Line 47, "alkoxylaled" should read -- alkoxylated --.
Line 59, "Schwartt" should read -- Schwartz --.
Lines 65-66, "monobydroxy" should read -- monohydroxy --.

UNITED STATES PATENT AND TRADEMARK OFFICE
CERTIFICATE OF CORRECTION

PATENT NO.   : 6,753,063 B1
DATED        : June 22, 2004
INVENTOR(S)  : D. J. Pung et al.

It is certified that error appears in the above-identified patent and that said Letters Patent is hereby corrected as shown below:

Column 7,
Line 4, "bydroxypropyl" should read -- hydroxypropyl --.
Line 7, "oleyidi" should read -- oleyldi --.
Line 10, "trioxaheptadecyidiethylamine" should read -- trioxaheptadecyldiethylamine --.
Line 11, "2-dodecoxyethyidimethylamine" should read -- 2-dodecoxyethyldimethylamine --.
Line 13, "dimethylhexadecylaamine" should read -- dimethylhexadecylamine --.
Line 20, "Aimghoteric" should read -- Amphoteric --.
Line 29, "amidines" should read -- amines --.
Line 46, "iminodialkanoatea" should read -- iminodialkanoates --.
Line 49, "alphboxyethl" should read -- alphacarboxyethyl --.
Line 51, "Lonizaine" should read -- Lonzaine --.
Line 52, "cabbozymethyl" should read -- carboxymethyl --.
Line 54, "alpharboxyethyl" should read -- alpha-carboxyethyl --.
Line 60, "coeamidopropyl" should read -- cocamidopropyl --.

Column 8,
Lines 56-57, "arninoalkanoates" should read -- aminoalkanoates --.

Column 9,
Line 5, "PG-ditwonium" should read -- PG-dimonium --.
Line 7, "NTC" should read -- PTC --.
Line 25, "$R_1$" should read -- $R_2$ --.
Line 48, "12to" should read -- 12 to --.

Column 10,
Lines 1 and 6, "anunonium" should read -- ammonium --.
Line 4, "disallow" should read -- ditallow --.
Lines 22 and 23, "disallow" should read -- ditallow --.
Line 26, the first occurrence of "disallow" should read -- ditallow --.
Line 26, the second occurrence of "disallow" should read -- ditallow --.
Lines 27-28, "anmmonium" should read -- ammonium --.
Lines 28, "anmmonium" should read -- ammonium --.
Lines 30 and 35, "stearamnidopropyl" should read -- stearamidopropyl --.
Line 39, "anmnonium" should read -- ammonium --.

UNITED STATES PATENT AND TRADEMARK OFFICE
CERTIFICATE OF CORRECTION

PATENT NO. : 6,753,063 B1
DATED : June 22, 2004
INVENTOR(S) : D. J. Pung et al.

It is certified that error appears in the above-identified patent and that said Letters Patent is hereby corrected as shown below:

Column 11,
Line 7, "beat" should read -- heat --.
Line 42, "arm" should read -- are --.
Line 43, "bed" should read -- heat --
Line 56, "47-49" should read -- 47-69 --.
Line 60, "petroleum" should read -- petrolatum --.

Column 12,
Lines 8 and 14, "petroleum" should read -- petrolatum --.
Line 17, "arn" should read -- are --.
Line 26, "isododocane" should read -- isododecane --.
Line 67, "pentaoleate" should read -- pentaletate --.

Column 13,
Line 45, "nonliniting" should read -- nonlimiting --.
Line 49, "Coming® 225" should read -- Corning® 225 --.
Line 51, "Coming® 200" should read -- Corning® 200 --.
Line 59, "Coming® 593" should read -- Corning® 593 --.

Column 14,
Line 49, "sot" should read -- not --.

Column 15,
Line 17, "filly" should read -- fully --.
Line 29, "nepivacaine" should read -- mepivacaine --.
Line 35, "phospbo-DOPA" should read -- phospho-DOPA--.

Column 16,
Line 34, "4-N,N-(2ethylhexyl)" should read -- 4-N,N-(2-ethylhexyl) --.
Line 39, "2-hydroxy442-hydroxyethoxy)benzophenone" should read
-- 2-hydroxy-4-(2-hydroxyethoxy)benzophenone --.

UNITED STATES PATENT AND TRADEMARK OFFICE
CERTIFICATE OF CORRECTION

PATENT NO. : 6,753,063 B1
DATED : June 22, 2004
INVENTOR(S) : D. J. Pung et al.

It is certified that error appears in the above-identified patent and that said Letters Patent is hereby corrected as shown below:

Column 17,
Line 5, "nonexclusive" should read -- non-exclusive --.
Line 10, "thereof" should read -- thereof. --.
Line 56, "anmmonium" should read -- ammonium --.

Column 18,
Line 39, "flagrance" should read -- fragrance --.
Line 42, "arm" should read -- are --.

Column 20,
Line 16, "6%" should read -- 60% --.
Line 50, "ad" should read -- and --.

Signed and Sealed this

First Day of March, 2005

JON W. DUDAS
*Director of the United States Patent and Trademark Office*